United States Patent [19]

Bühler et al.

[11] 4,260,544
[45] Apr. 7, 1981

[54] HALOGENOMETHYLENE-INDOXYLS

[75] Inventors: Niklaus Bühler, Rheinfelden; Hans Bosshard, Basel; Alfred Sallmann, Bottmingen, all of Switzerland

[73] Assignee: Ciba-Geigy Corporation, Ardsley, N.Y.

[21] Appl. No.: 876,375

[22] Filed: Feb. 9, 1978

[30] Foreign Application Priority Data

Feb. 11, 1977 [LU] Luxembourg ............................ 76754

[51] Int. Cl.³ .............................................. C07D 209/18
[52] U.S. Cl. ................... 260/326.13 C; 260/326.13 F
[58] Field of Search ............... 260/326.13 C, 326.13 F Primary Examiner—Donald G. Daus
Assistant Examiner—D. B. Springer
Attorney, Agent, or Firm—Luther A. R. Hall

[57] ABSTRACT

Novel halogenomethylene-indoxyls [halogeno-(3-oxa-[2H]- indol-2-ylidene)-acetic acids] and a novel process for their preparation by reacting N-acylanilides with dihalogenomaleic anhydrides or derivatives thereof are described. The novel halogenomethylene-indoxyls are valuable intermediates for the preparation of pharmaceutical active compounds having anti-allergic properties.

16 Claims, No Drawings

HALOGENOMETHYLENE-INDOXYLS

The present invention relates to novel halogenomethylene-indoxyls [halogeno-(3-oxa-[2H]-indol-2-ylidene)-acetic acids] and a novel process for their preparation.

The novel halogenomethylene-indoxyls are of the formula I

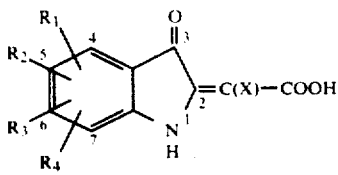

in which X is chlorine, bromine or fluorine and in which either $R_1$ is a lower alkyl group, a halogen atom or a hydroxyl, lower alkoxy, phenoxy or cycloalkyl group, $R_2$ is hydrogen or a lower alkyl, lower alkoxy or hydroxyl group and $R_3$ and $R_4$ independently of one another are hydrogen or a lower alkyl group and at least one of $R_1$ to $R_4$ is a lower alkyl group bonded to the benzene ring in the 5-position or 6-position, or $R_1$ and $R_2$ together are alkylene having 3-5 carbon atoms which is bonded to two adjacent carbon atoms and $R_3$ and $R_4$ are hydrogen.

The compounds according to the invention can be in the form of the cis or the trans isomers or in the form of mixtures of cis/trans isomers relative to the exocyclic C=C double bond. Mixtures of isomers of this type can be separated into their constituents on the basis of the differences in the physicochemical properties, in a conventional manner, for example by chromatography or by fractional crystallisation.

The compounds of the formula I can be prepared in high purity in a simple and economic manner using readily accessible starting materials and under mild reaction conditions, by reacting a compound of the formula II

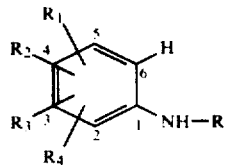

in the presence of a Lewis acid with a compound of the formula III

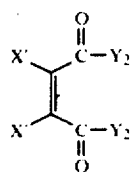

to give a compound of the formula IV

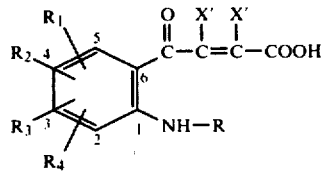

and subsequently cyclising the compound of the formula IV to a compound of the formula I, the group R being detached. In the above formulae II-IV, $R_1$, $R_2$, $R_3$ and $R_4$ are as defined under formula I, R is an acyl group, the two X' independently of one another are chlorine, fluorine or bromine and one of $Y_1$ and $Y_2$ is halogen, especially chlorine or bromine, and the other is —OH or —O—alkyl having 1-6 C atoms, or $Y_1$ and $Y_2$ together form the grouping —O—. If $R_1$ is a lower alkyl group, a halogen atom or a hydroxyl, lower alkyl, phenoxy or cycloalkyl group, $R_2$ is hydrogen or a lower alkyl, lower alkoxy or hydroxyl group and $R_3$ and $R_4$ independently of one another are hydrogen or a lower alkyl group, at least one of $R_1$ to $R_4$ in formula II and IV is a lower alkyl group bonded to the benzene ring in the 3-position or 4-position.

X and X' are preferably bromine and especially chlorine. $Y_1$ and $Y_2$ together preferably form the grouping —O—.

Lower alkyl groups as $R_1$ to $R_4$ and lower alkoxy groups as $R_1$ and $R_2$ have in particular 1-7 and preferably 1-4 carbon atoms, such as the methyl, ethyl, n-propyl, isopropyl, n-butyl, n-pentyl, n-heptyl, methoxy, ethoxy, n-propoxy, isopropoxy, n-butoxy, n-pentyloxy and n-hexyloxy group. Particularly preferred lower alkyl and lower alkoxy groups have 1 to 2 carbon atoms, in particular the methyl group and the methoxy group.

If $R_1$ is a halogen atom, this is in particular halogen having an atomic number of up to and including 35, i.e. fluorine, bromine and especially chlorine.

Preferred cycloalkyl groups $R_1$ are unsubstituted cycloalkyl groups having 5 to 8 ring carbon atoms, such as the cyclopentyl, cycloheptyl and cyclooctyl group and in particular the cyclohexyl group.

Phenoxy groups $R_1$ are preferably unsubstituted but can also be substituted by lower alkyl or lower alkoxy groups having 1-4 and especially 1 or 2 carbon atoms, such as the methyl or methoxy group, or by halogen atoms, for example chlorine.

Alkylene having 3 to 5 carbon atoms which is formed by $R_1$ and $R_2$ together is expecially 1,3-propylene or 1,4-butylene or, less preferentially, 1,5-pentylene.

Acyl groups R are, for example, aliphatic or aromatic acyl groups, especially alkanoyl groups having up to 6 carbon atoms, such as the formyl, acetyl, propionyl, butyryl and valeroyl group, and also the benzoyl group. R is preferably the acetyl group.

Preferred compounds of the formula I are those in which X is a chlorine atom and either $R_1$ is a lower alkyl group having 1-4 carbon atoms, a halogen atom having an atomic number of up to and including 35, a hydroxyl group, a cycloalkyl group having 5-7 carbon atoms, especially cyclohexyl, or a lower alkoxy group having 1-4 carbon atoms and $R_2$, $R_3$ and $R_4$ independently of one another are hydrogen or a lower alkyl group having 1-4 carbon atoms and at least one of the radicals $R_1$, $R_2$, $R_3$ and $R_4$ is a lower alkyl group having 1-4 carbon atoms which is bonded in the 5-position or 6-position, or in which $R_1$ and $R_2$ together are alkylene having 3 to 5 carbon atoms which is bonded in the 5,6-position and $R_3$ and $R_4$ are hydrogen.

Particularly preferred compounds are those of the formula Ia

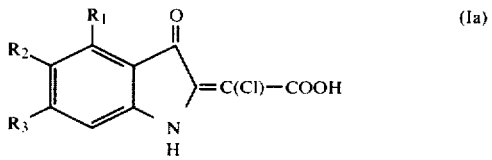

in which either one of the radicals $R_2$ and $R_3$ is lower alkyl having 1-4 carbon atoms, for example methyl, one of the remaining radicals $R_1$, $R_2$ and $R_3$ is hydrogen, lower alkyl having 1-4 carbon atoms, for example methyl, halogen having an atomic number of up to and including 35, for example chlorine, —OH or lower alkoxy having 1-4 carbon atoms, for example methoxy, and the last of the radicals $R_1$, $R_2$ and $R_3$ is hydrogen or lower alkyl having 1-4 carbon atoms, for example methyl, or in which $R_1$ is hydrogen and $R_2$ and $R_3$ together are alkylene having 3 or 4 carbon atoms, for example 1,3-propylene.

Very particularly preferred compounds are those of the formula Ia in which $R_1$ is hydrogen or methyl and one of the radicals $R_2$ and $R_3$ is methyl and the other is hydrogen or methyl, or in which $R_1$ is hydrogen and $R_2$ and $R_3$ together are trimethylene.

The starting compounds of the formula II and III are known per se or can be prepared by conventional methods. Compounds of the formula III which are preferably used are those in which the two X' have the same meaning and $Y_1$ and $Y_2$ together are the grouping —O—, and especially dichloromaleic anhydride.

Examples of Lewis acids which can be used when reacting the compounds of the formula II with the compounds of the formula III are: aluminium chloride, aluminium bromide, zinc chloride, tin tetrachloride, boron trifluoride, iron-III chloride, phosphorus trichloride, phosphorus oxychloride, antimony pentafluoride, antimony pentachloride and titanium tetrachloride. Aluminium chloride is preferably used.

The Lewis acid is appropriately employed in excess, for example in about 2 times to 10 times the molar amount. The reactants of the formula II and III are preferably employed in substantially stoichiometric amounts.

The reaction to give the intermediates of the formula IV can be carried out in an inert organic solvent or in the melt. Suitable organic solvents are, for example: chlorinated aliphatic or aromatic hydrocarbons, such as methylene chloride, 1,2-dichloroethane, 1,2,3-trichloropropane, 1,1,2,2-tetrachloroethane and o-dichlorobenzene; n-pentane and n-hexane; nitrobenzene, nitromethane and carbon disulphide.

The reaction in the melt is appropriately carried out in the presence of low-melting salt mixtures, for example mixtures of aluminium chloride with inorganic or organic salts, such as ammonium halides, alkaline earth metal halides and alkali metal halides, for example ammonium chloride, magnesium chloride and calcium chloride, but especially sodium chloride and potassium chloride, and also pyridinium salts, for example N-alkyl-pyridinium halides. Eutectic salt mixtures, especially mixtures of aluminium chloride and sodium chloride and/or potassium chloride, are preferred. However, in themselves any desired salt mixtures can be employed if an adequate lowering of the melting point is achieved therewith.

However, the reaction is preferably carried out in an inert organic solvent, especially methylene chloride, 1,2-dichloroethane or 1,1,2,2-tetrachloroethane.

In general, the reaction temperatures are between about 0° and 130° C. For the reaction in an inert organic solvent, reaction temperatures of between about 0° and 90° C. are preferred, depending on the nature of the solvent. In most cases, however, the reaction in the presence of an inert organic solvent can already be carried out at temperatures of between about 0° and 60° C.

The reaction in the melt is appropriately carried out at temperatures of between about 70° and 120° C. After the reaction has ended, the resulting complex is appropriately decomposed by pouring it into a water/ice mixture or by adding a dilute mineral acid, such as hydrochloric acid, with cooling, and the solvent, if present, is removed.

In most cases, the intermediates of the formula IV can be isolated, and purified, in a manner which is conventional per se. However, isolation and purification of this type is not necessary.

The cyclisation of the compounds of the formula IV with elimination of HX and detaching of the protective group R can be carried out in an organic or aqueous-organic medium. However, the cyclisation is preferably carried out in an aqueous medium.

The cyclisation temperature and time can vary greatly depending on the nature of the intermediate of the formula IV and of the reaction medium chosen.

Mixtures of a base, such as pyridine or triethylamine, with suitable inert organic solvents and, if desired, water are appropriately used for the cyclisation in an organic or aqueous-organic medium. Suitable inert organic solvents are, for example, aliphatic or aromatic hydrocarbons, which can be chlorinated, such as 1,2-dichloroethane, benzene, toluene and chlorobenzene; aliphatic or cyclic ethers, such as diethyl ether, tetrahydrofurane and dioxane; ethylene glycol monoalkyl and dialkyl ethers having, in each case, 1-4 carbon atoms in the alkyl parts, such as ethylene glycol monomethyl ether and ethylene glycol monoethyl ether, ethylene glycol dimethyl ether and ethylene glycol diethyl ether; or cellosolve.

In some cases the cyclisation can even be carried out in a weakly acid to neutral aqueous medium (pH between about 4 and 7) and at a temperature of between about 0° and 100° C.

Preferably, the cyclisation is carried out in an aqueous medium on its own or in an aqueous medium in the presence of an organic or inorganic base. Examples of bases which can be used are tertiary amines, such as triethylamine, pyridine, pyridine bases or alkali metal hydroxides or carbonates and alkaline earth metal hydroxides or carbonates. Alkaline earth metal hydroxides and carbonates and alkali hydroxides and carbonates are preferred, especially sodium hydroxide and potassium hydroxide and the corresponding carbonates. The reaction temperatures are appropriately between about 0° and 100° C. and preferably between about 0° and 60° C.

According to a particularly preferred embodiment, the cyclisation is carried out in an aqueous medium with the addition of, advantageously, about 2 to 6 mols of an alkali metal hydroxide, especially sodium hydroxide or potassium hydroxide, per mol of intermediate of the formula IV at a temperature of between about 0° and 40° C. It is surprising that, although it has a high reactivity towards nucleophilic agents, the second halogen atom is not also detached in the cyclisation, according to the invention, in an alkaline medium.

After the reaction has ended, the compounds of the formula I can be isolated in a conventional manner, for example by acidifying the reaction mixture with hydrochloric acid or other mineral acids and by filtering and washing with water. The compounds of the formula I obtained by the process according to the invention in general contain only slight impurities and can be used direct for preparative purposes. If desired, they can be converted to the analytically pure form by recrystallisation from suitable solvents, such as anhydrous acetic acid, ethyl acetate, methanol, ethanol, dioxane or toluene.

The halogenomethylene-indoxyls are obtained in the form of red to blackish crystals and are valuable intermediates for the preparation of pharmaceutical active compounds having an antiallergic action, for example 3-hydroxy-indolyl-2-glyoxylic acids and esters or salts thereof. The preparation of several pharmaceutical active compounds which have antiallergic properties and can be used, for example, for the treatment and prophylaxis of allergic diseases, such as asthma, hay fever, conjunctivitis, urticaria and eczema, is described in the examples.

EXAMPLE 1

200 ml of 1,2-dichloroethane and 350 g (2.625 mols) of powdered anhydrous AlCl₃ are initially introduced into a stirred flask provided with a HCl outlet, and cooled to 0° C. using an external ice bath. Subsequently, in the course of about 30 minutes, with stirring, 100 g (0.61 mol) of 3,4-dimethylacetanilide in 200 ml of 1,2-dichloroethane and, thereafter, in the course of 10 minutes, 102 g (0.58 mol) of solid dichloromaleic anhydride (95% pure) are added at 0°-10° C. After stirring thoroughly at 20°-25° C. for 30 minutes, the reaction mixture is stirred for a further 22 hours at 40° C. The reaction mixture is then introduced into a mixture of water and ice (end volume about 3-4 liters). The water is then decanted off and the brown-yellow oily residue is stirred with 1,000 ml of ethyl acetate and filtered off with suction. The material on the suction filter is dried at 50° C. in a vacuum drying cabinet. This gives 165.5 g of a yellow product. 600 ml of 10% strength aqueous NaOH are added to this product and the mixture is cooled with ice in such a way that the reaction temperature does not exceed 32° C. After stirring for 5½ hours at 20°-25° C., the reaction mixture is warmed to 40° C. for one hour. After cooling again to 20°-25° C., the resulting red suspension is filtered with suction. The red crystals (39 g) thus obtained are gently dried, after intensive washing with water, at 40° C. in vacuo. The pH of the mother liquor is adjusted to 1 with concentrated HCl and the resulting red precipitate is filtered off with suction. After washing thoroughly with water, the material on the suction filter is dried. This gives 90 g of red crystals which are identical to the first crystalline product. The total yield is 129 g or 84.3% of theory.

According to the thin layer chromatogram, the product contains only slight impurities and can therefore be used direct for further reactions.

NMR spectrum (100 megahertz, δ value in ppm, solution in DMSOd₆): 2.15 (s, 6H, 2 CH₃); 3.5 (s broad, 1H, NH, disappears on the addition of D₂O); 6.9 (s, 1H, aromatic); 7.2 (s 1H, aromatic); 10.15 (s broad, 1H, COOH, disappears on the addition of D₂O).

The spectroscopic findings from NMR, MS, IR and UV correspond to the formula

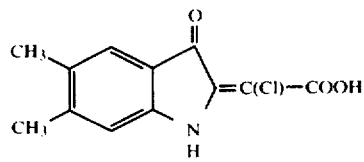

[2-carboxychloromethylene-5,6-dimethyl-indoxyl or chloro-(5,6-dimethyl-3-oxy-[2H]-indol-2-ylidene)-acetic acid].

EXAMPLE 2

2-carboxychloromethylene-5,6-dimethyl-indoxyl can also be prepared as follows:

60 g (0.45 mol) of powdered anhydrous AlCl₃ in 30 ml of 1,2-dichloroethane are initially introduced into an apparatus of the type described above and cooled to 0° C. with an external ice bath. 16.3 g (0.1 mol) of 3,4-dimethylacetanilide in 30 ml of 1,2-dichloroethane are then added in the course of about 30 minutes at 0°-10° C. After stirring for 30 minutes at 0° C., 21.8 g (0.1 mol) of the acid chloride of monomethyl 2,3-dichloromaleate are added dropwise at 0°-10° C. The reaction mixture is stirred at room temperature for 15 hours and then poured onto 500 g of ice. The resulting yellow suspension is filtered with suction and the material on the suction filter is washed with 50 ml of ethyl acetate and dried at 60° C. in a vacuum drying cabinet. This gives 26.2 g of a yellow solid. This is dissolved in 100 ml of 10% strength aqueous sodium hydroxide solution, with ice-cooling, and the solution is stirred under a nitrogen atmosphere for 24 hours at room temperature and then diluted with 200 ml of water and the undissolved constituents are separated off. The pH of the filtrate is adjusted to 2 with concentrated hydrochloric acid and the resulting red precipitate is filtered off with suction and dried in a vacuum drying cabinet at 60° C. This gives 17.6 g (69.8% of theory) of red crystals which are identical to the product obtained according to Example 1. The ester group present in the starting material is saponified under the indicated reaction conditions.

EXAMPLES 3-8

Further compounds of the formula I which have been prepared by the process described in Example 1 are listed in the table which follows:

| Ex. | Compound of the formula II | ![structure] X-C(=O)-O-C(=O)-X with substituents | Solvent | Reaction time hours | temperature °C. |
|---|---|---|---|---|---|

-continued

| Ex. | (structure) | X | Solvent | Time (h) | Temp (°C) |
|---|---|---|---|---|---|
| 3 | (indane)-NHCOCH₃ | X = Cl | 1,2,-dichloroethane | 0.5, 3.5 | 20-25, 40 |
| 4 | (CH₃)₂CH-C₆H₄-NH-COCH₃ | " | " | 1 | 50 |
| 5 | CH₃-C₆H₄-NHCOCH₃ | " | " | 15 | 40 |
| 6 | CH₃-C₆H₄-NHCOCH₃ | " | 1,1,2,2-tetrachloroethane | 3 | 60 |
| 7 | C₂H₅-C₆H₄-NHCOCH₃ | " | 1,2-dichloroethane | 24 | 20-25 |
| 8 | (CH₃)₂-C₆H₃-NHCOCH₃ | X = Br | " | 15 | 20-25 |

| Ex. | Compound of the formula I | Recrystallised from | Melting point °C./yield % of theory |
|---|---|---|---|
| 3 | (indane fused)-CO-NH-C=C(Cl)-COOH | glacial acetic acid | 200° decomposition 73% |
| 4 | (CH₃)₂CH-C₆H₃(CO-NH)-C=C(Cl)-COOH | " | 124° decomposition |
| 5 | CH₃-C₆H₃(CO-NH)-C=C(Cl)-COOH | — | 195° decomposition |
| 6 | CH₃-C₆H₃(CO-NH)-C=C(Cl)-COOH | — | decomposition |
| 7 | C₂H₅-C₆H₃(CO-NH)-C=C(Cl)-COOH | — | 150-150° decomposition |
| 8 | (CH₃)₂-C₆H₂(CO-NH)-C=C(Br)-COOH | — | >250° C. |

EXAMPLE 9

20.0 g of the 5,6-dimethyl-2-carboxychloromethylene-indoxyl prepared according to Example 1 are reacted in 280 ml of ethanol with 13.6 g of piperidine for 3 hours at 50° C., with stirring, and the reaction mixture is then diluted to 750 ml with ice and water. After adding 50 ml of concentrated hydrochloric acid, the product is filtered off and dissolved in 800 ml of water with the addition of 50 ml of 30% strength sodium hydroxide solution and the solution is clarified by filtration. The filtrate is rendered acid to congo red with hydrochloric acid and the 5,6-dimethyl-3-hydroxy-indolyl-2-glyoxylic acid of the formula

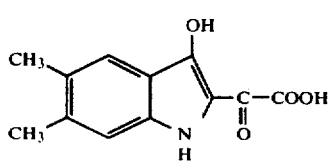

which has separated out is filtered off, washed with water and dried. After recrystallisation from glacial acetic acid it has a melting point of 238° C. (decomposition).

The same product can also be prepared in the following way:

5.0 g of 5,6-dimethyl-2-carboxychloromethylene-indoxyl in 42 ml of dimethylsulphoxide and 8 ml of water are kept at 75° C. for 16 hours, with stirring, 150 ml of water are then added and the mixture is filtered. The product is dissolved in 300 ml of water with the addition of 20 ml of 30% strength sodium hydroxide solution, the solution is clarified by filtration and the filtrate is rendered acid to congo red by adding hydrochloric acid. The crude product which has separated out is purified as described above.

EXAMPLE 10

251.5 g (1.0 mol) of the 5,6-dimethyl-2-carboxychloromethylene-indoxyl [chloro-(5,6-dimethyl-3-oxa[2H]indol-2-ylidene)-acetic acid] prepared according to Example 1 are suspended in 1,300 ml of water and the pH of the suspension is adjusted to 7 with concentrated sodium hydroxide solution. 378 g (3.0 mols) of dimethyl sulphate are then added in the course of 6 hours at 20°-25° C., the pH value being controlled by a pH-stat and kept at 6.8-7.2 by the dropwise addition of 10% strength sodium carbonate solution. After stirring at this pH for 20 hours, the crude suspension is filtered and the material on the filter is washed well with water and dried at 60° C. and 100 mm Hg. 5,6-dimethyl-2-methoxycarbonylchloromethylene-indoxyl [methyl chloro-(5,6-dimethyl-3-oxy[2H]-indol-2-ylidene)-acetate] of the formula

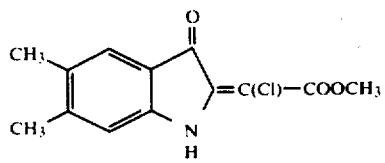

is thus obtained as red crystals which melt at 208°-210° C. Recrystallisation from glacial acetic acid raises the melting point to 215°-218° C.

79.7 ml of piperidine are added dropwise to a suspension of 98.0 g of 5,6-dimethyl-2-methoxycarbonylchloromethylene-indoxyl in 1,500 ml of ethanol at room temperature (20°-25° C.), with stirring. The mixture is stirred for 30 minutes at room temperature and for 18 hours at 60° C. It is then concentrated to dryness under reduced pressure, 200 ml of water and 1,000 ml of ethyl acetate are added to the residue, the mixture is shaken thoroughly and the organic phase is separated off and again washed with 100 ml of water. It is then dried over magnesium sulphate and evaporated to dryness under reduced pressure. The crystalline residue is chromatographed on 2,000 g of silica gel. Fractions 17-23, which are each eluted with 1,000 ml of diethyl ether, contain the pure 5,6-dimethyl-2-(α-methoxycarbonyl)-piperidinomethylene-indoxyl [methyl (5,6-dimethyl-3-oxa[2H]-indol-2-ylidene)-piperidino-acetate].

These fractions are combined and triturated with 100 ml of diethyl ether. The product which has crystallised out melts at 170°-173° C.

A solution of 7.0 g of 5,6-dimethyl-2-(α-methoxycarbonyl)-piperidinomethylene-indoxyl in 80 ml of 10% strength sulphuric acid is stirred for 30 minutes at 60° C. and cooled. The crystals which have separated out are filtered off, washed with 20 ml of water and dried under 0.01 mm Hg at 40° C. After recrystallisation from methanol, methyl 5,6-dimethyl-3-hydroxy-indolyl-2-glyoxylate melts at 188°-192° C.

EXAMPLE 11

Methyl 3-hydroxy-5,6-trimethylene-indoxyl-2-glyoxylate with a melting point of 200°-202° C. can be prepared in a manner analogous to that described in the preceding Example 10, starting from 2-carboxychloromethylene-5,6-trimethylene-indoxyl (compound according to Example 2), via 5,6-trimethylene-2-methoxycarbonylchloromethylene-indoxyl with a melting point >220° C. and 2-(α-methoxycarbonyl)-piperidinomethylene-5,6-trimethylene-indoxyl with a melting point of 166°-168° C.

USE EXAMPLES (A) Tablets containing 0.1 g of active compound, for example methyl 5,6-dimethyl-3-hydroxy-indolyl-2-glyoxylate, are prepared as follows:

Composition (for 1,000 tablets)

active compound, 100 g
lactose, 50 g
wheat starch, 73 g
colloidal silica, 13 g
magnesium stearate, 2 g
talc, 12 g
water, q.s.

The active compound is mixed with a portion of the wheat starch and with the lactose and the colloidal silica and the mixture is forced through a sieve. A further portion of the wheat starch is mixed to a paste with five times the amount of water on a water bath and the above powder mixture is kneaded with this paste until a slightly plastic mass has formed. The plastic mass is pressed through a sieve of about 3 mm mesh width and dried and the dry granules are again forced through a sieve. The remaining wheat starch, the talc and the magnesium stearate are then mixed in and the resulting mixture is pressed to give tablets of 0.25 g.

(B) An approximately 2% strength aqueous solution, which is suitable for inhalation, of an active compound which is water-soluble in the free form or in the form of the sodium salt can be prepared, for example, in the following composition:

Composition active compound, for example methyl 3-hydroxy-5,6-trimethylene-indoxyl-2-glyoxylate, 2,000 mg
stabiliser, for example the sodium salt of ethylenediaminetetracetic acid, 10 mg
preservative, for example benzalkonium chloride, 10 mg
water, freshly distilled to make up to 100 ml The active compound is dissolved in freshly distilled water with the addition of the equimolar amount of 2 N sodium hydroxide solution. The stabiliser and the preservative are then added. After all of the components have dissolved completely, the resulting solution is made up to 100 ml and filled into small bottles and these are sealed gas-tight.

What is claimed is:
1. A compound of formula Ia

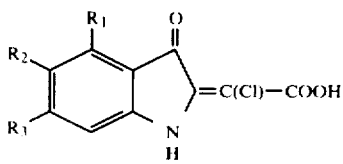
(Ia)

wherein $R_1$ is hydrogen, $R_2$ is methyl and $R_3$ is chloro, or $R_2$ is bromo and $R_3$ is methyl; or $R_2$ and $R_3$ are methyl; or wherein $R_1$ is methyl, $R_2$ is hydrogen, and $R_3$ is methyl; or wherein $R_1$ and $R_2$ are hydrogen and $R_3$ is methyl or ethyl; or wherein $R_1$ and $R_3$ are hydrogen, and $R_2$ is methyl, ethyl, isopropyl or n-butyl; or wherein $R_1$ is hydrogen, and $R_2$ and $R_3$ together are alkylene having 3 carbon atoms.

2. A compound according to claim 1 wherein $R_1$ is hydrogen, and $R_2$ and $R_3$ are methyl; or $R_1$ and $R_3$ are hydrogen, and $R_2$ is methyl, ethyl or isopropyl; or $R_1$ and $R_2$ are hydrogen, and $R_3$ is methyl; or $R_1$ is hydrogen, and $R_2$ and $R_3$ together are trimethylene.

3. A compound of formula Ia according to claim 1, in which $R_1$ is hydrogen or methyl and one of $R_2$ and $R_3$ is methyl and the other is hydrogen or methyl, or in which $R_1$ is hydrogen and $R_2$ and $R_3$ together are trimethylene.

4. A compound according to claim 1 of the formula

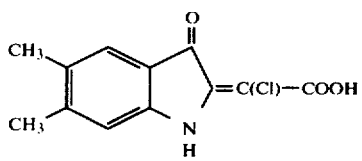

5. A compound according to claim 1 of the formula

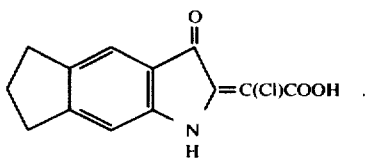

6. The compound 2-carboxybromomethylene-5,6-dimethylindoxyl,

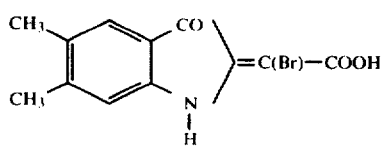

7. A process for the preparation of a compound of formula Ib

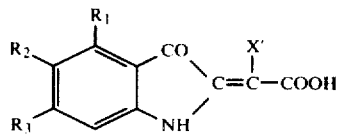

wherein $R_1$ is hydrogen, $R_2$ is methyl and $R_3$ is chloro, or $R_2$ is bromo and $R_3$ is methyl; or $R_2$ and $R_3$ are methyl; or wherein $R_1$ is methyl, $R_2$ is hydrogen, and $R_3$ is methyl; or wherein $R_1$ and $R_2$ are hydrogen, and $R_3$ is methyl or ethyl; or wherein $R_1$ and $R_3$ are hydrogen, and $R_2$ is methyl, ethyl, isopropyl or n-butyl; or wherein $R_1$ is hydrogen, and $R_2$ and $R_3$ together are alkylene having 3 carbon atoms; and $X'$ is chlorine or bromine, which consists essentially of
reacting a compound of formula IIb

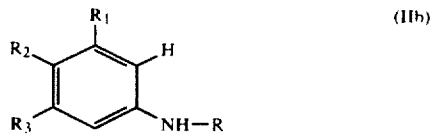

wherein $R_1$, $R_2$ and $R_3$ are defined as above and $R$ is alkanoyl having 1-6 carbon atoms or benzoyl, in substantially stoichiometric amounts with a compound of formula III

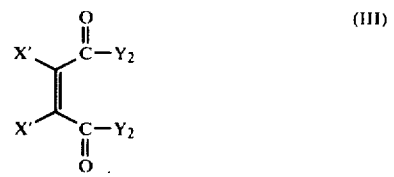

wherein the two X's independently of one another are chlorine or bromine, and one of $Y_1$ and $Y_2$ is halogen and the other is —OH or —O—alkyl having 1-6 carbon atoms; or $Y_1$ and $Y_2$ together form the grouping —O—; in the melt or in an inert organic solvent selected from the group consisting of chlorinated aliphatic hydrocarbons, chlorinated atomatic hydrocarbons, n-pentane, n-hexane, nitrobenzene, nitromethane and carbon disulfide, at a temperature between about 0° and 130° C. in the presence of an excess molar amount of a Lewis acid selected from the group consisting of aluminum chloride, aluminum bromide, zinc chloride, tin tetrachloride, boron trifluoride, ferric chloride, phosphorus trichloride, phosphorus oxychloride, antimony pentafluoride, antimony pentachloride and titanium tetrachloride to give a compound of formula IVb

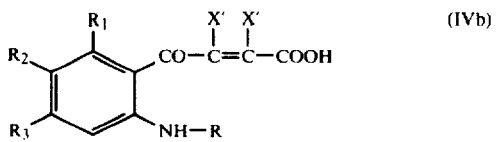

wherein $R_1$, $R_2$, $R_3$, R and $X'$ are as defined above; in the reaction mixture; and then
adding the reaction mixture containing the compound of formula IVb to an aqeuous medium at a temperature between about 0° and 100° C. to give the compound of formula Ib.

8. A process according to claim 7 where $R_1$ is hydrogen and $R_2$ and $R_3$ are methyl; or $R_1$ and $R_3$ are hydrogen, and $R_2$ is methyl, ethyl or isopropyl; or $R_1$ and $R_2$ are hydrogen, and $R_3$ is methyl; or $R_1$ is hydrogen, and $R_2$ and $R_3$ together are trimethylene.

9. A process according to claim 7 where the compound of formula III is dichloromaleic anhydride, dibromomaleic anhydride or the acid chloride of monomethyl 2,3-dichloromaleate.

10. A process according to claim 7 wherein $R_1$ is hydrogen and $R_2$ and $R_3$ are methyl; and the compound of formula III is dichloromaleic anhydride, dibromomaleic anhydride or the acid chloride of monomethyl 2,3-dichloromaleate.

11. A process according to claim 7 wherein $R_1$ and $R_3$ are hydrogen and $R_2$ is methyl, ethyl or isopropyl; or $R_1$ and $R_2$ are hydrogen and $R_3$ is methyl; or $R_1$ is hydrogen, and $R_2$ and $R_3$ together are trimethylene; and the compound of formula III is dichloromaleic anhydride.

12. A process according to claim 7 wherein the aqueous medium to which the reaction mixture containing the compound of formula IVb is added consists essentially of water and an inert organic solvent selected from the group consisting of aliphatic hydrocarbons, aromatic hydrocarbons, chlorinated aliphatic hydrocarbons, chlorinated aromatic hydrocarbons, aliphatic ethers, cyclic ethers, ethylene glycol monoalkyl ethers and ethylene glycol dialkyl ethers.

13. A process according to claim 7 wherein the aqueous medium to which the reaction mixture containing the compound of formula IVb is added consists essentially of water and an organic or inorganic base.

14. A process according to claim 7, wherein dichloromaleic anhydride is used as the compound of the formula III.

15. A process according to claim 7, wherein a compound of the formula II is used in which R is the acetyl group.

16. A process according to claim 7, wherein the reaction is carried out in the presence of an inert organic solvent.

* * * * *